United States Patent [19]

Leach et al.

[11] Patent Number: 4,775,653

[45] Date of Patent: Oct. 4, 1988

[54] ALKOXYLATION PROCESS USING CALCIUM BASED CATALYSTS

[75] Inventors: Bruce E. Leach; Mark L. Shannon; Donald L. Wharry, all of Ponca City, Okla.

[73] Assignee: Vista Chemical Company, Houston, Tex.

[21] Appl. No.: 43,660

[22] Filed: Apr. 28, 1987

[51] Int. Cl.[4] .......................... B01J 31/04; B01J 31/02
[52] U.S. Cl. .................................. 502/170; 502/171; 568/618
[58] Field of Search ................................ 502/170, 171

[56] References Cited

U.S. PATENT DOCUMENTS 3,244,646  4/1966  Naro et al. ...................... 502/171 X

FOREIGN PATENT DOCUMENTS 26547   4/1981  European Pat. Off. ............ 502/171
104309  4/1984  European Pat. Off. ............ 502/171
148726  11/1979 Japan ................................... 502/171

Primary Examiner—Patrick P. Garvin
Attorney, Agent, or Firm—Browning, Bushman, Zamecki & Anderson

[57] ABSTRACT

A process for preparing an alkoxylation catalyst in which the catalyst pre-mix is formed by admixing an alkoxylated alcohol with a calcium containing compound which is dispersible in the alkoxylated alcohol, an inorganic acid and an aluminum trialkoxide, the pre-mix being heated to a temperature and for a time sufficient to effect at least partial exchange reaction between the alkoxide groups of the aluminum alkoxide and the hydroxyl groups of the alkoxylated alcohol. There is also disclosed and claimed an alkoxylation process utilizing the catalysts formed as described above.

11 Claims, No Drawings

ALKOXYLATION PROCESS USING CALCIUM BASED CATALYSTS

BACKGROUND OF THE INVENTION

1. Field of the Invention

The present invention relates to a process for the preparation of alkylene oxide adducts of active hydrogen compounds such as alcohols and to a process for preparing catalysts useful in such alkoxylation reactions.

2. Description of the Prior Art

Alkylene oxide adducts of hydrogen compounds find utility in a variety of products such as, for example, surfactants, solvents, chemical intermediates, etc. Typically, these alkylene oxide adducts are prepared by an addition or alkoxylation reaction in which an alkylene oxide, such as ethylene oxide, is reacted under suitable conditions with an organic compound, such as an alcohol, having one or more active hydrogen atoms. In particular, ethylene oxide adducts of aliphatic alcohols or substituted phenols having from about 8 to 20 carbon atoms have found widespread utility as non-ionic detergent components of cleaning formulations for use in industry and in the home.

The alkoxylation reaction produces a product mixture of various alkoxylate molecules having a variety of alkylene oxide adducts (oxyethylene adducts). Because the number of oxyalkylene adducts or oxyalkylene groups affect the properties of the product, it is desirable to tailor the adduct number distribution of a given product mixture to its intended service. For example, it is known that in surfactant applications, an adduct with too few ethylene oxide molecules is not effective because of poor water solubility, while an adduct with too many ethylene oxide molecules is undesirable because surface tension reduction per unit mass decreases drastically with increasing molecular weight. Thus, as taught in U.S. Pat. No. 4,239,917, it is desirable, particularly for surfactant applications, to use ethoxylates or alkoxylates with a narrow distribution in the desired mole adduct range of from about 5 to about 10 alkylene oxide adducts per alkylate molecule.

PCT Application WO85/00365 discloses an alkoxylation process which utilizes a calcium based catalyst to produce alkoxylation products having a narrow distribution of alkoxylation species.

U.S. Pat. No. 3,941,606 discloses compositions useful as siccatives in paints and composed of the reaction product of a polyvalent metal compound such as an oxide of calcium, a branched chain aliphatic or a non-aromatic cyclic acid, and a polyol or alkoxy alkanol.

SUMMARY OF THE INVENTION

It is therefore an object of the present invention to provide a novel process for preparing calcium based alkoxylation catalysts having enhanced activity.

It is further an object of the present invention to produce a calcium based catalyst for alkoxylation reactions which is stable and sows increased activity with aging.

Another object of the present invention is to provide a process for preparing alkoxylation product mixtures having narrow alkoxylation product distributions.

The above and other objects of the present invention will become apparent from the description given herein and the appended claims.

In one aspect, the present invention provides a process for preparing an alkoxylation catalyst in which a catalyst pre-mix is formed by admixing an alkoxylated alcohol, a calcium containing compound which is at least partially dispersible in the alkoxylated alcohol, an inorganic acid and an aluminum alkoxide, the calcium compound being added prior to addition of the aluminum alkoxide. The catalyst pre-mix is then heated to a temperature and for a time sufficient to effect at least a partial exchange reaction between the alkoxide groups of the aluminum alkoxide and the hydroxyl group of the alkoxylated alcohol to thereby form an active alkoxylation catalyst. In another aspect, the present invention provides a process for the alkoxylation of an alcohol in which the active alkoxylation catalyst prepared by the method described above is used in a process wherein an alcohol reactant and an alkylene oxide are brought together, in the presence of the alkoxylation catalyst and under typical alkoxylation conditions, to thereby produce alkoxylated derivatives of the alcohol reactant.

DETAILED DESCRIPTION OF THE PREFERRED EMBODIMENT

In preparing the alkoxylation catalyst according to the process of the present invention, a catalyst pre-mix is first formed by admixing an alkoxylated alcohol, a calcium containing compound which is at least partially dispersible in the alkoxylated alcohol, an inorganic acid and an aluminum alkoxide. The alkoxylated alcohols useful in forming the catalyst are those having the general formula $R_1-O+CH_2-CH_2-O+_nH$ where $R_1$ is a hydrocarbon radical containing from 1 to about 30 carbon atoms and n is an average and is from about 2 to about 20. Particularly useful are alkoxylated alcohols wherein $R_1$ is from about 8 to about 14, most preferably from about 10 to about 12. In preferred alkoxylated alcohols, n is from about 1 to about 12, most preferably from about 1 to about 4. Thus, ethoxylates of fatty alcohols such as decanol and dodecanol wherein there are from about 1 to 12 and most preferably from 1 to 4 moles of ethylene oxide are especially preferred. The $R_1$ group is generally an organic residue of an aliphatic alcohol which may be of branched or straight chain structure, although preferably, particularly for surfactant use, it is preferred that greater than 50%, more preferably greater than 60% and most preferably greater than 70% of such alcohol molecules are of linear (straight chain) carbon structure.

Specific examples of primary, straight chain monohydric aliphatic alcohols from which the $R_1$ group can be derived include ethanol, hexanol, octanol, decanol, dedecanol, tetradecanol, pentadecanol, octadecanol, eicosanol, etc. Examples of branched chain or secondary alcohols from which the $R_1$ group can be derived include isopropanol, isoheptanol, 3-heptanol, isodecanol, 2-methyl-1-nonanol, 2-methyl-1-undecanol, 4-tetradecanol and 4-hexadecanol.

The alkoxylated alcohols used in the catalyst forming process of the present invention can be prepared by methods well known in the art for preparing ethylene oxide adducts of alcohols. Alternately, the ethylene oxide adducts can be prepared according to the process of the present invention.

The calcium containing compound used in the process of the present invention is one which is at least partially dispersible in the alkoxylated alcohol. As used herein, the term "dispersible" refers to a calcium compound which solublizes or otherwise interacts with the alkoxylated alcohol in such a manner that it becomes a new species of calcium compound. It is to be understood, however, that inasmuch as the mechanism is not completely understood, the term "dispersible" or "soluble" is not intended to be limited to the formation of a truly dissolved calcium species as would be commonly understood in the case of ordinary solublization. While compounds such as calcium hydride, calcium acetate, calcium oxalate, calcium nitrate, etc. may be used, it is preferred that the calcium containing compound be calcium oxide, calcium hydroxide or a mixture thereof.

The inorganic acids useful in the process of the present invention include the acids themselves as well as "acid salts". Thus, non-limiting examples of inorganic acids include sulphuric acid, hydrochloric acid, hydrofluoric acid, phosphoric acid, pyrophosphoric acid, ammonium biflouride, ammonium sulfate, etc. Particularly preferred are the oxy acids, such as sulphuric acid.

The aluminum alkoxide used in the process of the present invention will have the general formula

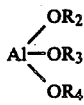

wherein $R_2$, $R_3$ and $R_4$ is each a hydrocarbon radical containing from about 1 to about 30 carbon atoms. Generally speaking, the description set out above with respect to the $R_1$ radical is generally applicable to the $R_2$ radical, i.e., the $R_2$ radical is generally an organic residue derived from an alcohol. Desirably, the aluminum trialkoxide is obtained by reacting an aluminum trialkyl with ethylene followed by oxidation which produces aluminum alkoxides in which the chain length of the groups $R_2$, $R_3$ and $R_4$ vary. It will be appreciated that while the groups $R_2$, $R_3$ and $R_4$ can each be, and generally are, different from one another, they may all be the same. It is generally preferred to use aluminum alkoxides wherein each of the $R_2$, $R_3$ and $R_4$ groups is such as to provide an average chain length of from about 8 to about 14 carbon atoms for all of the $R_2$, $R_3$ and $R_4$.

In preparing the catalyst pre-mix, relative amounts of the various components can vary widely. For example, the mole ratio of the calcium compound to the aluminum alkoxide can vary from about 1:1 to about 10:1, based on calcium and aluminum, respectively. The mole ratio of the inorganic acid to the aluminum alkoxide can vary from about 0.25:1 to abut 4:1, based on the ratio of the acid equivalent e.g. acid hydrogens, in the inorganic acid to the aluminum, respectively. It is generally preferred that the combined concentration of the calcium compound, the inorganic acid and the aluminum alkoxide be present in the catalyst pre-mix in an amount of from about 1 to about 10% by weight, the alkoxylated alcohol and diluents such as free alcohol being present in an amount of from about 90-99% by weight. Depending on the source and type of the alkoxylated alcohol, free alcohol content can range from about 1% by weight to about 60% by weight.

Generally speaking, the order of addition of the various components of the catalyst pre-mix is immaterial with the exception that the calcium compound must be added prior to addition of the aluminum alkoxide. Thus, although it is common practice in carrying out the process of the present invention to admix the alkoxylated alcohol, the calcium compound and the inorganic acid, followed by the addition of the aluminum alkoxide, the process can also be carried out by reversing the order of addition of the aluminum alkoxide and the inorganic acid.

In addition to the above components of the catalyst pre-mix, the pre-mix can contain, with advantage, organic acids. Suitable organic acids are those carboxylic acids which have greater miscibility in hydrocarbon solvents than in water. Such carboxylic acids, which may generally be considered fatty acids, have a carbon chain length versus acid functionality which provides the greater miscibility or acid functionality which provides the greater miscibility or solubility in hydrocarbons. Non-limiting examples of fatty acids include those natural or synthetic mono-functional carboxylic acids wherein the carbon chain length is greater than about 5 carbon atoms, generally from about 5 to about 15 carbon atoms. Specific examples of such suitable acids include hexanoic, octanoic, nonanoic, 2-ethyl hexanoic, neodecanoic, isooctanoic, stearic, napthanoic, and mixtures or isomers of such acids. While it is preferred that the acids, if used, be saturated, they may optionally contain other functional groups such as hydroxyl groups, amine groups, etc. which do not interfere with the process. It has been found that the use of the fatty acids leads to a better dispersion of the calcium compound and that the active catalyst suspension is more stable in terms of the solids remaining dispersed.

In preparing the catalyst according to the process of the present invention, a typical alkoxylated alcohol is admixed with a suitable calcium containing compound such as calcium oxide and the mixture stirred for a suitable period of time until at least some of the calcium compound disperses or solublizes in the alkoxylated alcohol. Generally, this is accomplished by stirring, or other means of agitation to achieve intimate and thorough contact, at a temperature of generally from about 25° C. to about 150° C. (usually below the boiling point of the alkoxylated alcohol) for a sufficient period of time. The dispersion time can vary from about 0.5 hours to about 20 hours. As can be seen, longer times can be used if desired. Once the dispersion has been formed, as evidenced, e.g., by the pressure of titratible alkalinity, the inorganic acid is then slowly or incrementally added. The aluminum alkoxide is then added and stirring of the mixture continued and the mixture heated to a temperature and for a sufficient period of time to effect at least a partial exchange reaction between the alkoxide groups of the aluminum alkoxide and the hydroxyl group of the alkoxylated alcohol.

The precise temperature to which the catalyst pre-mix is heated will, of course, depend upon the nature of the components employed to form the pre-mix. However, as noted above, the heating of the catalyst pre-mix to activate it is usually carried out at a temperature and for a period of time sufficient to effect at least a partial exchange reaction between the alkoxide groups of the aluminum alkoxide and the hydroxyl group of the alkoxylated alcohol. This point can generally be determined by the evolution of alcohol which distills out of the mixture. While catalyst activation occurs to some extent with any heating in the desired range, activation is best evidenced by the evolution of alcohol as a result of the exchange reaction. However, in order to achieve a highly active catalyst, it is preferred that the heating be carried on until the mixture has reached a substantially constant boiling point. The desired activation temperature should, for a given pressure, approximate the boiling point of a substantial fraction of the free alcohols derived from the $R_2$, $R_3$ and $R_4$ group of the aluminum alkoxide. At this point, maximum exchange has likely occurred between the alkoxide groups of the aluminum alkoxide and the hydroxyl group of the alkoxylated alcohol. It will be recognized that when the aluminum alkoxide utilized is one where $R_2$, $R_3$ and $R_4$ are long chain, e.g. 10 to 14 carbon atoms and longer, the alcohols produced in the exchange reaction are high boiling. Accordingly, very little if any distillation of alcohol occurs without the application of extremely high temperatures which can cause unwanted side reactions. In such cases, the heating can be carried out to a temperature of about 190°-300° C. and more preferably from about 230°-260° C. Lower temperatures may be employed when the process is conducted under reduced pressure, e.g. at a pressure of about 150-300 Torr, temperature in the range of about 160° C. to about 210° C. are suitable. Indeed, it has been found that reduced pressure results in highly potent catalysts. For a given catalyst pre-mix, the desired temperature range can be determined by sampling the catalyst dispersion as it is being heated at various times during the heating cycle and subjecting the samples to an ethoxylation reaction. When the desired degree of activity is achieved in the ethoxylation reaction, heating can be discontinued and all future catalyst pre-mix of the same composition heated to that temperature, and, of course, for that period of time. Generally, however, the time of heating can vary from about 0.1 hour to about 5 hours, generally in the range of from about 0.2 hour to about 1 hour.

It has been found that if after the catalyst is prepared it is aged, e.g., by allowing it to stand at room temperature, activity can be greatly enhanced. Although the aging time for a given catalyst pre-mix will, of course, depend upon the components of that pre-mix, the desired aging time can be determined in a manner similar to that described above with respect to determining the desired temperature and time of heating. Thus, samples of the catalyst which are being aged can be used in ethoxylation reactions and the degree of activity determined. Generally aging times ranging from about two hours to about one week or longer can be used.

It has been found that in order to make highly active catalysts, it is preferred that when the catalyst pre-mix is being formed, any water which is present should be removed prior to the addition of the aluminum alkoxide regardless of whether the aluminum alkoxide is added before or after the addition of the inorganic acid.

To more fully demonstrate the present invention, the following non-limiting examples are presented:

EXAMPLE 1

400 grams of an ethoxylated alcohol known as ALFONIC 1412-40[1] marketed by Vista Chemical Company was sparged with nitrogen for one hour. To this ethoxylated alcohol was added 30.27 grams of calcium oxide prepared by the calcination of calcium hydroxide at 600° C. for 12 hours. This mixture was then stirred at 90° C. for 16 hours. To this dispersion was added 80.9 grams of an aluminum trialkoxide in which the alkoxide groups have an average chain length of 10 carbon atoms (mixed 2-30 carbon chain length) and containing 6% by weight of aluminum. This mixture was stirred for an additional one hour at 90° C. Concentrated sulphuric acid (18.2 grams) was then added drop wise and the mixture heated to 240° C. as light alcohol and trace water were distilled overhead. The mixture was cooled and tested for activity.

[1]Mixture of 60% by wt. $C_{14}$ alcohol and 40% by wt. $C_{12}$ alcohol with 40% by wt. ethylene oxide adduct.

EXAMPLE 2

The catalyst prepared by Example 1 was tested for activity in making alcohol ethoxylates. In preparing the ethoxylates, a 60 weight percent tetradecanol/40 weight percent dodecanol mixture was employed as the reactant alcohol. The ethoxylation reaction was conducted at 175° C. and 40 psig ethylene oxide pressure. The amount of activated catalyst present was such as to provide approximately 0.5 grams of metal (calcium plus aluminum) during the reaction. The results are shown below in Table I:

TABLE I

| Reaction Time | Percent E.O. Used | Percent Free Alcohol | Percent 0-5 Mole Adducts | Average Moles E.O. | Hydroxyl Number |
|---|---|---|---|---|---|
| 1.74 hr. | 69.72 | 0.14 | 1.49 | 10.74 | 90.0 |

EXAMPLE 3

A highly active ethoxylation catalyst was prepared by the addition of 37.75 grams of calcium hydroxide to 500 grams of ALFONIC 1412-40 alcohol ethoxylate which had been purged with nitrogen for 0.5 hours. The mixture was stirred for 24 hours at 95° C. Sulphuric acid (17.25 grams) was added and 0.5 hour later, 128.1 grams of an aluminum alkoxide specially prepared by exchange of aluminum triisopropoxide with a mixed $C_{12}/C_{14}$ alcohol containing approximately 60% by weight $C_{14}$ alcohol and approximate 40% by weight $C_{12}$ alcohol. This mixture was then heated to 240° C. bottoms temperature for about 30 minutes. There was very little overhead fraction collected. The catalyst Sample 3-1 thus prepared was used to ethoxylate various alcohols. In addition, the level of catalyst required was varied in order to test the activity. With this catalyst, it was found that the activity became so high after approximately one week of aging at room temperature that the initial stage of the ethoxylation was too vigorous at an ethoxylation oxide pressure of 40 psig. Accordingly, it was necessary to initiate the ethoxylation at only 25 psig, raising the pressure gradually to 40 psig after approximately 40 to 50% of the reaction was completed. The results are given below in Table II.

TABLE II

| Catalyst Age | Catalyst Amount Used | Reactant Alcohol Used | Percent E.O. Desired | Reaction Time | Percent E.O. Used | Percent Alcohol |
|---|---|---|---|---|---|---|
| Fresh | 10.0 g | 60% wt $C_{14}$ 40% wt $C_{12}$ | 70 | 1.17 hr. | 69.0 | 0.12 |
| 1 Week | 5.0 g | 60% wt $C_{14}$ 40% wt $C_{12}$ | 70 | 1.00 hr. | 69.8 | 0.04 |
| 1 Week | 2.5 g | 60% wt $C_{14}$ 40% wt $C_{12}$ | 70 | 1.84 hr. | 69.3 | 0.08 |
| 2 Week | 10.0 g | 60% wt $C_8$ 40% wt $C_{10}$ | 60 | 0.95 hr. | 59.9 | 1.90 |

TABLE II-continued

| Catalyst Age | Catalyst Amount Used | Reactant Alcohol Used | Percent E.O. Desired | Reaction Time | Percent E.O. Used | Percent Alcohol |
|---|---|---|---|---|---|---|
| 2 Week | 5.0 g | 60% wt $C_{14}$ 40% wt $C_{12}$ | 60 | 0.99 hr. | 60.2 | 0.59 |
| 2 Week | 5.0 g | 60% wt $C_{10}$ 40% wt $C_{12}$ | 60 | 1.07 hr. | 59.1 | 1.60 |

As a point of reference with respect to Table II, 10.0 grams of the catalyst provides approximately 0.5 grams of metal (calcium plus aluminum) to the reaction and the total amount of ethoxylate produced is 300 grams per batch. Thus, the loading of metal to ethoxylate product required is less than 0.17 weight percent. It can be seen that the best activity in terms of reaction time was obtained by using approximately 0.09 weight percent metal to ethoxylate ratios.

As can be seen, the catalyst produced in this example shows greater activity in terms of reaction time than the catalyst produced pursuant to Example 1. Thus, aging of the catalyst affects the activity. In addition, it should be noted that using the catalyst produced by the process of the present invention, the free alcohol content of the ethoxylates is quite low. This is important in the manufacture of surfactants since high free alcohol leads to odor problems. Moreover, it is important that spray-dried ethoxylate not plume. High free alcohol in the ethoxylates contributes to pluming.

EXAMPLE 4

500 grams of ALFONIC 1412-40 ethoxylated alcohol was purged with nitrogen and heated to 90° C. 37.75 grams of calcium oxide was added and the mixture stirred for 24 hours. Sulphuric acid (17.25 grams) was added and the mixture stirred for an hour. A sample of the catalyst (Sample 4-1) was taken at this point in the preparation and found to be inactive. Aluminum alkoxide prepared from a mixture of about 60% by weight tetradecanol and about 40% by weight dodecanol was added to a portion of Sample 4-1 catalyst. In addition of the aluminum alkoxide had no effect as the Sample 4-1 catalyst remained inactive. The remaining catalyst, without the aluminum compound added, was then heated to 240° C. for about 30 minutes. A sample of this catalyst (Sample 4-2) was taken and found to be inactive in a standard ethoxylation run. The addition of more sulphuric acid to Sample 4-2 up to twice the normal quantity previously used and with further heating to 240° C. also resulted in an inactive catalyst (Sample 4-3). This example shows that the catalyst, using calcium oxide as the calcium compound, is inactive prior to the addition of the aluminum alkoxide and heat treatment of the mixture.

EXAMPLE 5

To determine if the inactive catalyst Sample 4-2 which did not contain aluminum alkoxide could be activated by the addition of aluminum alkoxide and heating, 86.2 grams of Sample 4-2 was added to a reaction vessel and admixed with 20.5 grams of aluminum alkoxide made from a mixture of about 60% by weight $C_{14}$ alcohol and 40% by weight $C_{12}$ alcohol. The temperature was increased to 240° C. (bottoms temperature) and the catalyst tested for activity. The catalyst was now found to be active for ethoxylation. This catalyst was used in an ethoxylation run using an alcohol mixture comprised of about 60% by weight tetradecanol and about 40% by weight dodecanol at 175° C. and a 40 psig ethylene oxide pressure. The reaction time was 4.24 hours. The free alcohol was found to be 0.06 weight percent and the hydroxyl number was 96.0.

EXAMPLE 6

To 400 grams of ALFONIC 1412-40 ethoxylated alcohol was added 100 grams of isopropanol and 32.5 grams of aluminum triisopropoxide. The isopropanol was distilled overhead to a bottoms temperature of 240° C. Calcium oxide (30.2 grams) was added and the mixture stirred overnight at a temperature of 90° C. Sulphuric acid (13.8 grams) was added and stirring continued at 90° C. for 0.5 hours. The temperature was then increased to 240° C. and held for 15 minutes at that temperature. The catalyst mixture was cooled and tested for ethoxylation activity and found to be inactive. This example shows that in the process it is necessary that the calcium compound be added prior to addition of the aluminum alkoxide to obtain an active catalyst.

EXAMPLE 7

This example demonstrates that the catalyst is much more active if the calcium compound and the ethoxylated alcohol are stirred or otherwise agitated for a sufficient period of time in forming the catalyst pre-mix. Two preparations were compared, Sample 7-1 and Sample 7-2. Each preparation had the same ingredients in common. However, Sample 7-2 was stirred 16 hours at 90°-100° C. while Sample 7-1 was stirred 3 hours at 150° C. in an attempt to compensate temperature for time. In the preparations, 300 grams of ALFONIC 1412-70[2] and 100 grams of ALFONIC 1412-40 alcohol ethoxylates were mixed. To this mixture were added 30.2 grams of calcium oxide. The stirring times designated were accomplished prior to adding 80.9 grams of the aluminum alkoxide used in Example 1, stirring 0.5 hours and the addition of 13.6 grams of sulphuric acid followed by heating to a bottoms temperature of 240° C. Sample 7-1 showed only slight ethoxylation activity whereas sample 7-2 was highly active for ethoxylation. Sample 7-2, run under normal ethoxylation conditions, gave 2.21 and 2.2 hour reaction times, free alcohols of 0.15 and 0.12 weight percent and hydroxyl numbers of 88.0 and 89.0. The actual levels of ethylene oxide incorporation for 70 weight percent normal ethoxylate were 68.62 and 69.63 weight percent with the average moles of ethylene oxide per alcohol chain being 10.20 and 10.70, respectively. On the other hand, catalyst preparation 7-1 was virtually inactive for alcohol ethoxylation, no ethylene oxide update being observed after initiation or after waiting for one hour.

[2]Mixture of 60% by weight $C_{14}$ alcohol and 40% by weight $C_{12}$ alcohol with 70% by weight ethylene oxide adduct.

EXAMPLE 8

500 grams of ALPHONIC 1412-40 alcohol ethoxylate containing 5 to 10 grams of water was added to a two liter stirred flask. 28.8 grams of nonanoic acid was added immediately and the mixture heated to 100° C.

with stirring. Calcium hydroxide (43.5 grams) was added and the mixture stirred for 16 hours at 100° C. Sulphuric acid (9.0 grams) was added and the mixture then heated to 170° C. to distill out water. At this point 85.0 grams of the aluminum alkoxide used in Example 1 was added and a nitrogen purge started. The temperature was increased to 240° C. and held there for 30 minutes as alcohol distilled out. The reaction product was then cooled. This catalyst sample was designated Sample 8-1. Table III shows ethylene oxide adduct distributions for ethoxylated alcohol made by reacting ethylene oxide with a mixture of about 60% by weight tetradecanol and 40% by weight dodecanol using catalyst Samples 8-1 and Sample 3-1.

As can be seen from Table III, using the catalyst with the nonanoic acid, the ethylene oxide adduct distribution shows an average maximum component level below that obtained using catalyst Sample 3-1, i.e. without any nonanoic or other fatty acid. In other words, there is a flattening of the distribution using the catalyst incorporating the fatty acid. However, in certain surfactant applications, such a broader distribution can be advantageous.

of nonanoic acid, 3 grams water and 87 grams of calcium hydroxide and heating at 95° C. for 16 hours. The mixture was then sparged with nitrogen and heated to 200° C. to remove water. A 330 gram aliquot of the calcium pre-mix was mixed with 7.0 grams of sulphuric acid and 65 grams of the aluminum alkoxide used in Example 1 and heated under partial vacuum (220 mm) to 195° C. where alcohol began to distill overhead. It was found that 10 grams of the above catalyst mixture ethoxylated 90 grams of an alcohol (60% $C_{14}$/40%$C_{12}$) to a 70% ethoxylate at 175° in 51 minutes. It was found that the catalyst was so active under these conditions that regulation of ethylene oxide into the reactor was initially necessary for temperature control. This example demonstrates the desirable effects achieved by conducting the heating of the catalyst pre-mix under reduced pressures. Specifically, it can be seen that by using reduced pressure activation, the catalysts run faster but produce the same quality of ethoxylates in terms of the content of free alcohols.

TABLE III

| ALCOHOL ETHOXYLATED | PERCENT E.O. | SAMPLE NO. | PERCENT WITH GIVEN MOLES E.O. | | | | | | | | | | | |
|---|---|---|---|---|---|---|---|---|---|---|---|---|---|---|
| | | | 0 | 1 | 2 | 3 | 4 | 5 | 6 | 7 | 8 | 9 | 10 | 11 |
| 1412GC | 69.69 | 8-1 | 0.02 | 0.01 | 0.04 | 0.05 | 0.14 | 0.37 | 1.03 | 2.64 | 5.99 | 10.79 | 13.43 | 17.81 |
| 1412GC | 69.04 | 8-1 | 0.04 | 0.00 | 0.03 | 0.05 | 0.19 | 0.52 | 1.43 | 3.59 | 7.65 | 12.74 | 16.83 | 17.84 |
| 1412GC | 69.90 | 3-1 | 0.14 | 0.00 | 0.02 | 0.02 | 0.09 | 0.20 | 0.55 | 1.71 | 4.79 | 10.34 | 16.51 | 20.22 |
| 1412GC | 70.17 | " | 0.12 | 0.00 | 0.01 | 0.02 | 0.10 | 0.23 | 0.61 | 1.83 | 4.90 | 10.54 | 16.54 | 20.02 |
| 1412GC | 70.45 | " | 0.04 | 0.00 | 0.02 | 0.05 | 0.09 | 0.21 | 0.57 | 1.74 | 4.63 | 9.81 | 15.50 | 19.26 |
| 1412GC | 70.57 | " | 0.08 | 0.01 | 0.02 | 0.07 | 0.09 | 0.20 | 0.54 | 1.60 | 4.34 | 9.39 | 15.16 | 19.03 |
| 1412GC | 70.70 | " | 0.17 | 0.00 | 0.01 | 0.02 | 0.08 | 0.17 | 0.45 | 1.36 | 3.89 | 8.82 | 14.78 | 19.22 |
| 1412GC | 69.38 | " | 0.09 | 0.00 | 0.02 | 0.03 | 0.14 | 0.36 | 1.03 | 2.85 | 6.60 | 12.06 | 16.79 | 18.59 |
| 1412GC | 69.38 | " | 0.09 | 0.01 | 0.02 | 0.03 | 0.14 | 0.37 | 1.05 | 2.88 | 6.65 | 12.00 | 16.78 | 18.51 |
| 1412GC | 69.55 | " | 0.10 | 0.01 | 0.03 | 0.04 | 0.15 | 0.38 | 1.02 | 2.72 | 6.26 | 11.47 | 16.17 | 18.22 |
| 1412GC | 69.76 | " | 0.18 | 0.00 | 0.01 | 0.02 | 0.09 | 0.25 | 0.75 | 2.22 | 5.33 | 10.77 | 16.84 | 18.82 |
| 1412GC | 69.90 | " | 0.09 | 0.01 | 0.02 | 0.03 | 0.12 | 0.31 | 0.02 | 2.30 | 3.32 | 10.34 | 15.49 | 18.20 |
| 1412GC | 69.26 | " | 0.11 | 0.00 | 0.01 | 0.02 | 0.10 | 0.35 | 1.02 | 2.81 | 6.70 | 12.43 | 17.48 | 19.22 |
| 1412GC | 69.97 | " | 0.07 | 0.01 | 0.02 | 0.03 | 0.15 | 0.37 | 0.97 | 2.50 | 5.59 | 10.27 | 14.74 | 17.34 |
| 1412GC | 69.19 | " | 0.00 | 0.01 | 0.05 | 0.04 | 0.16 | 0.42 | 1.20 | 3.20 | 7.07 | 12.27 | 16.89 | 18.38 |
| 1412GC | 68.64 | " | 0.07 | 0.02 | 0.05 | 0.07 | 0.17 | 0.50 | 1.48 | 3.93 | 8.48 | 14.00 | 18.04 | 18.21 |
| 1412GC | 69.88 | " | 0.05 | 0.01 | 0.02 | 0.03 | 0.04 | 0.17 | 0.58 | 1.91 | 5.23 | 10.71 | 16.59 | 19.61 |
| 1412GC | 69.33 | " | 0.11 | 0.01 | 0.02 | 0.03 | 0.07 | 0.23 | 0.79 | 2.56 | 6.34 | 12.46 | 17.80 | 19.49 |
| 1412GC | 69.15 | " | 0.15 | 0.01 | 0.03 | 0.05 | 0.16 | 0.44 | 1.24 | 3.25 | 7.15 | 12.40 | 16.79 | 10.10 |
| AVERAGE | 69.72 | 8-1 | 0.10 | 0.01 | 0.02 | 0.03 | 0.12 | 0.30 | 0.84 | 2.43 | 5.00 | 11.20 | 16.34 | 18.83 |
| AVERAGE | 69.30 | 8-1 | 0.03 | 0.00 | 0.03 | 0.05 | 0.17 | 0.44 | 1.23 | 3.12 | 6.82 | 11.74 | 16.13 | 17.83 |

| ALCOHOL ETHOXYLATED | PERCENT E.O | SAMPLE NO. | PERCENT WITH GIVEN MOLES E.O. | | | | | | | | | | |
|---|---|---|---|---|---|---|---|---|---|---|---|---|---|
| | | | 12 | 13 | 14 | 15 | 16 | 17 | 18 | 19 | 20 | 21 | 22 |
| 1412GC | 69.69 | 8-1 | 16.49 | 12.74 | 8.22 | 4.55 | 2.19 | 0.89 | 0.32 | 0.11 | 0.04 | 0.01 | |
| 1412GC | 69.04 | 8-1 | 15.39 | 10.95 | 6.50 | 3.41 | 1.57 | 0.65 | 0.22 | 0.15 | 0.09 | 0.05 | 0.02 |
| 1412GC | 69.90 | 3-1 | 18.11 | 13.65 | 7.95 | 3.62 | 1.44 | 0.47 | 0.13 | 0.03 | | | |
| 1412GC | 70.17 | " | 18.02 | 13.42 | 7.83 | 3.62 | 1.43 | 0.49 | 0.14 | 0.05 | | | |
| 1412GC | 70.45 | " | 13.97 | 8.58 | 4.33 | 1.81 | 0.64 | 0.18 | 0.06 | | | | |
| 1412GC | 70.57 | " | 18.32 | 14.29 | 8.95 | 4.65 | 1.99 | 0.75 | 0.25 | 0.07 | 0.03 | | |
| 1412GC | 70.70 | " | 18.79 | 14.99 | 9.43 | 4.70 | 2.02 | 0.76 | 0.24 | 0.05 | | | |
| 1412GC | 69.38 | " | 16.34 | 11.79 | 7.06 | 3.57 | 1.60 | 0.65 | 0.26 | 0.11 | 0.03 | 0.02 | |
| 1412GC | 69.38 | " | 16.29 | 11.68 | 7.00 | 3.60 | 1.65 | 0.71 | 0.31 | 0.14 | 0.04 | 0.03 | |
| 1412GC | 69.55 | " | 16.47 | 12.23 | 7.58 | 4.01 | 1.88 | 0.79 | 0.32 | 0.13 | 0.05 | | |
| 1412GC | 69.76 | " | 17.42 | 12.94 | 7.97 | 4.11 | 1.00 | 0.70 | 0.25 | 0.09 | 0.02 | | |
| 1412GC | 69.90 | " | 17.05 | 13.03 | 8.31 | 4.49 | 2.12 | 0.91 | 0.39 | 0.15 | 0.06 | 0.03 | |
| 1412GC | 69.26 | " | 16.50 | 11.27 | 6.48 | 3.17 | 1.35 | 0.54 | 0.22 | 0.08 | 0.03 | | |
| 1412GC | 69.97 | " | 16.68 | 13.24 | 8.82 | 4.99 | 2.46 | 1.09 | 0.43 | 0.16 | 0.06 | | |
| 1412GC | 69.19 | " | 14.04 | 11.42 | 6.75 | 3.44 | 1.53 | 0.62 | 0.24 | 0.10 | 0.04 | 0.02 | 0.01 |
| 1412GC | 68.64 | " | 14.77 | 9.87 | 5.50 | 2.71 | 1.18 | 0.50 | 0.20 | 0.09 | 0.05 | 0.02 | 0.01 |
| 1412GC | 69.88 | " | 17.99 | 13.07 | 7.71 | 3.77 | 1.59 | 0.40 | 0.21 | 0.07 | 0.05 | 0.01 | |
| 1412GC | 69.33 | " | 16.64 | 11.53 | 6.53 | 3.11 | 1.28 | 0.48 | 0.18 | 0.07 | 0.02 | | |
| 1412GC | 69.15 | " | 15.76 | 11.28 | 6.81 | 3.59 | 1.62 | 0.76 | 0.26 | 0.10 | 0.04 | 0.01 | |
| AVERAGE | 69.72 | 8-1 | 14.79 | 12.25 | 7.34 | 3.70 | 1.62 | 0.65 | 0.24 | 0.09 | 0.04 | 0.02 | 0.01 |
| AVERAGE | 69.30 | 8-1 | 15.94 | 11.85 | 7.40 | 3.90 | 1.80 | 0.77 | 0.27 | 0.13 | 0.04 | 0.03 | 0.018 |

EXAMPLE 9

A calcium compound dispersion was prepared by adding one kilogram of ALFONIC 1012-40, 16 grams

EXAMPLE 10

Samples of the catalysts made as per the procedure of Example 9 but using acids other than sulphuric acid were prepared. Thus, catalysts were prepared using hydrochloric acid, formic acid, ammonium bifluoride, carbonated aluminum alkoxide and boron trifluoride. While all of these catalysts showed some activity, they were found to be far less active than the catalyst prepared using sulphuric acid.

EXAMPLE 11

A calcium compound disperson was prepared by stirring 43.5 grams of calcium hydroxide in 500 grams of ALFONIC 1214-40 alcohol ethoxylate for 19 hours at 100° C. At this time, 9.2 grams of concentrated sulphuric acid was added slowly, with stirring, and the mixture stirred for an additional 5 hours. A 100 gram aliquot of this catalyst was removed and heated to 240° C. for thirty minutes to form the activated catalyst. Ten grams of this activated catalyst was used to ethoxylate 90 grams of a 60% $C_{14}$/40% $C_{12}$ alcohol. The ethoxylation reaction was conducted at a 40 psig ethylene oxide pressure at 175° C. to a 70% by weight ethylene oxide adduct produced. The ethoxylation data is shown in Table IV below.

TABLE IV

| Catalyst Age | Run Time | Free Alcohol | % Polyethylene Glycol | Dioxane |
|---|---|---|---|---|
| Fresh | 1.08 hrs | 0.25% | 0.63% | 10 ppm |
| 1 month | 1.53 hrs | 0.02% | 0.70% | <10 ppm |

EXAMPLE 12

A calcium compound dispersion was made and treated with concentrated sulphuric acid as in the Example above. Following that, 73.7 grams of aluminum alkoxide made from a 60% $C_{14}$/40% $C_{12}$ alcohol mixture was added and the entire mixture heated to 240° C. for thirty minutes to form the active catalyst. It was found that if this catalyst was used under the same conditions of pressure and temperature as was employed in Example 11 for ethoxylation reaction, the reaction could not be controlled. Indeed, the entire reaction was completed in 1.08 hours, including 10-15 minutes during which ethylene oxide addition was stopped to allow the temperature to lower. Because of temperature overruns, no analytical data was collected on the ethoxylate produced.

A second ethoxylation run was made with the catalyst prepared by Example 12 but this time using 5.0 grams of the catalyst mixture instead of 10 grams of catalyst mixture. The ethoxylation temperature was reduced to 150° C. to prevent overrun temperatures. While addition of ethylene oxide was allowed to proceed on demand, the rate of reaction was so rapid that pressure in the reactor did not reach 40 psig until 25 minutes into the run. The run was completed in 1.19 hours. The ethoxylation data is shown below in Table V.

TABLE V

| Free Alcohol | % Polyethylene Glycol | Dioxane |
|---|---|---|
| 0.05% | — | 30 ppm |

Examples 11 and 12 shown two important points. Number one, catalyst samples prepared using the aluminum alkoxide show greatly increased activity over those which do not contain the aluminum alkoxide. Additionally, it was observed that whereas catalysts which incorporate the aluminum alkoxide continue to improve with aging (see Example 3, Table II), catalysts prepared without the aluminum alkoxide showed decreased activity with aging (see Table IV).

The foregoing disclosure and description of the invention is illustrative and explanatory thereof, and various changes in the method steps may be made within the scope of the appended claims without departing from the spirit of the invention.

What is claimed is:

1. A process for preparing an alkoxylation catalyst comprising:
    forming a catalyst pre-mix by admixing an alkoxylated alcohol mixture containing an alkoxylated alcohol having the general formula $$R_1-O+(CH_2CH_2-O)_n H$$

wherein $R_1$ is a hydrocarbon radical containing from about 1 to about 30 carbon atoms and n is from about 1 to about 20 and from about 1 to about 60% by weight free alchohol, a calcium containing compound which is at least partially dispersible in said alkoxylated alcohol mixture, an inorganic acid selected from the class consisting of sulfuric acid, hydrochloric acid, hydrofluoric acid, phosphoric acid, pyrophosphoric acid, ammonium biflouride, ammonium sulfate, and mixtures thereof, and an aluminum alkoxide having the general formula

where $R_2$, $R_3$ and $R_4$ is each a hydrocarbon radical containing from about 1 to about 30 carbon atoms, said calcium containing compound and said alkoxylated alcohol mixture being mixed prior to addition of said aluminum alkoxide; and
    heating said catalyst pre-mix to a temperature and for a time sufficient to effect at least a partial exchange reaction between the alkoxide groups of said aluminum alkoxide and said hydroxyl group of said alkoxylated alcohol and thereby form an active alkoxylation catalyst.

2. The process of claim 1 wherein $R_1$ is a hydrocarbon radical containing from about 8 to about 14 carbon atoms.

3. The process of claim 1 wherein n is from about 1 to about 12.

4. The process of claim 1 wherein n is from about 1 to about 4.

5. The process of claim 1 wherein $R_2$, $R_3$ and $R_4$ is each a hydrocarbon radical containing from about 8 to about 14 carbon atoms.

6. The process of claim 1 wherein said calcium containing compound is selected from the group consisting of calcium oxide, calcium hydroxide and mixtures thereof.

7. The process of claim 1 wherein said inorganic acid is sulphuric acid.

8. The process of claim 1 wherein the mole ratio of said calcium containing compound to said aluminum alkoxide is from about 1:1 to about 10:1, calculated as calcium and aluminum, respectively.

9. The process of claim 1 wherein the mole ratio of said inorganic acid to said aluminum alkoxide is from about 0.25:1 to about 4:1, calculated as acidic hydrogen and aluminum, respectively.

10. The process of claim 1 including adding to said pre-mix a carboxylic acid wherein the carbon chain length is greater than about 5 carbon atoms.

11. The process of claim 1 including removing water from said pre-mix prior to the addition of said aluminum alkoxide.

* * * * *